(12) United States Patent
Beachy et al.

(10) Patent No.: US 7,276,370 B2
(45) Date of Patent: Oct. 2, 2007

(54) RF2A AND RF2B TRANSCRIPTION FACTORS

(75) Inventors: Roger N. Beachy, St. Louis, MO (US); Silvana Petruccelli, La Plata (AR); Shunhong Dai, St. Louis, MO (US)

(73) Assignee: Donald Danforth Plant Science Center, St. Louis, MO (US)

( * ) Notice: Subject to any disclaimer, the term of this patent is extended or adjusted under 35 U.S.C. 154(b) by 254 days.

(21) Appl. No.: 10/399,699

(22) PCT Filed: Oct. 23, 2001

(86) PCT No.: PCT/US01/50748

§ 371 (c)(1),
(2), (4) Date: Sep. 8, 2003

(87) PCT Pub. No.: WO02/46366

PCT Pub. Date: Jun. 13, 2002

(65) Prior Publication Data

US 2004/0073972 A1   Apr. 15, 2004

Related U.S. Application Data

(60) Provisional application No. 60/242,908, filed on Oct. 24, 2000.

(51) Int. Cl.
*C12N 15/82* (2006.01)
*C12N 15/00* (2006.01)
*C07H 21/04* (2006.01)

(52) U.S. Cl. .................. 435/320.1; 536/24.1; 435/468

(58) Field of Classification Search ..................... None
See application file for complete search history.

(56) References Cited

U.S. PATENT DOCUMENTS

| | | |
|---|---|---|
| 5,495,007 A | 2/1996 | Thompson et al. |
| 5,824,857 A | 10/1998 | Beachy et al. |
| 5,994,123 A | 11/1999 | Olszewski et al. |
| 6,013,884 A | 1/2000 | Rudolph et al. |

OTHER PUBLICATIONS

Yin et al. 1997, The EMBO Journal 16:5247-5259.*
Yin, Y. et al, RF2a, a bZIP transcriptional activator of the phloem-specific rice tungro bacilliform virus promoter, functions in vascular development. EMBO J. 1997, vol. 16, No. 17, pp. 5247-5259, see entire document.
Hi, X. et al. Contribution of downstream promoter elements to transcriptional regulation of the rice tungro bacilliform virus promoter. Nucleic Acids Research. Jan. 15, 2002, vol. 30, No. 2, pp. 497-508, see entire document.
Petruccelli, S. et al. Transcription factor RF2a alters expression of the rice tungro bacilliform virus promoter in transgenic tobacco plants. Proc. Natl. Acad. Sci. U.S. Jun. 19, 2001, vol. 98, No. 13, pp. 7635-7640, see entire document.

(Continued)

*Primary Examiner*—Ashwin Mehta
*Assistant Examiner*—Li Zheng
(74) *Attorney, Agent, or Firm*—Bryan Cave LLP (57) ABSTRACT

A method of activating the rice tungro bacilliform virus (RTBV) promoter in vivo is disclosed. The RTBV promoter is activated by exposure to at least one protein selected from the group consisting of Rf2a and Rf2b.

8 Claims, 7 Drawing Sheets

OTHER PUBLICATIONS

Dai, S. et al. The bacterial cytosine deaminase gene used as a conditional negative selection marker in transgenic rice plants. Plant Cell Reports. Dec. 2001, vol. 20, No. 8, pp. 738-743, see entire document.

He. X. et al. Sequence-specific and Methylation-dependent and independent Binding of Rice Nuclear Proteins to a Rice Tungro Bacilliform Virus Vascular Bundle Expression Element. J. Biol. Chem. Jan. 26, 2001, vol. 276, No. 4, pp. 2644-2651, see entire document.

He, X. et al. Transcriptional activation of rice tungro bacilliform virus gene is critically dependent on an activatory element located immediately upstream of the TATA box. J. Biol. Chem. Apr. 21, 2000, vol. 275, No. 16, pp. 11799-11808, see entire document.

Kloti, A. et al. Upstream and downstream sequence elements determine the specificity of the rice tungro bacilliform virus promoter and influence RNA production after transcription initiation. Plant Mol. Biol. May 1999, vol. 40, No. 2, pp. 249-266, see entire document.

Matsumara, T. et al. Transformation of rice plants by plan reovirus genes. Seminars in Biology, 1995, vol. 6, No. 2, pp. 133-139, see entire document.

Chen, G. et al. Efficient Transcription from the Rice Tungro Bacilliform Virus Promoter Requires Elements Downstream of the Transcription Start Site. J. Virology. Dec. 1996, vol. 70, No. 12, pp. 8411-8421, see entire document.

Database CAPLUS on STN, Accession No. 1997: 312197, (Scripps Research Institute, CA, USA), Yin, Y., Transcriptional regulation of the rice tungro bacilliform virus (RTBV) promoter in rice. Dissertation. Diss. Abstr. Int, B. 1996, 132 pages. 1997, vol. 57, No. 11, p. 6778, see entire document.

Battacharyya-Pakrasi, M. et al. Specificity of a promoter from the rice tungro bacilliform virus for expression in phloem tissues. Plant. J. Jul. 1993, vol. 4, No. 1, pp. 71-79, see entire document.

Yin, Y. et al. The regulatory regions of the rice tungro bacilliform virus promoter and interacting nuclear factors in rice (*Oryza sative L.*). Plant. J. Jun. 1995, vol. 7, No. 6, pp. 969-980, see entire document.

* cited by examiner

Schematic domain structure of RF2a (A) and RF2b (B)

```
RF2b      DPKRAKRILANRQSAARSKERKARYITELERKVQTLQTEATTLSAQLTLFQRDTTGLSAENAEL
B-ZIP     DPKRAKRIIANRQSAARSKERKARYILELERKVQTLQTEATTLSAQLSLFQRDTTGLSSENTEL
RF2a      DPKRAKRIWANRQSAARSKERKMRYIAELERKVQTLQTEATTLSAQLALLQRDTSGLTTENSEL
PosF21    DPKRAKRILANRQSAARSKERKTRYIFELERKVQTLQTEATTLSAQLTLLQRDTNGLTVENNEL
VSF-1     DPKRAKRILANRLSAARSKERKTRYISELEHKVQKLQTETTTLSTQVTILQKNFVEISSLNSEL

GBF1      ELKREKRKQSNRESARRSRLRKQAETEELATQVESLAAENTSLRSEIGRLTESSEKLRLENSAL
O2        EERVRKRKESNRESARRSRYRKAAHLKELEDQVAQLKAENSCLLRRIAALNQKYNDANVDNRVL
TGA1a     VEKVLRRLAQNREAARKSRLRKKAYVQQLENSKLKLIQLEQELERARKQGMCVGGGVDASQLSY·

Consensus ­­BB­BB­­­NR­SAABSB­BB­­­­­­LE­­­­­L­­­­­­L­­­­­­­L­­­­­­­L­­­­­­­­
```

Alignment of amino acid sequences in the bZIP domain of
RF2b and RF2a with other known bZIP proteins

FIGURE 7

RF2A AND RF2B TRANSCRIPTION FACTORS

CROSS REFERENCES TO RELATED APPLICATIONS

The present application is a §371 application of PCT/US01/50748, filed Oct. 23, 2001, which claims priority to U.S. provisional patent application Ser. No. 60/242,908, filed Oct. 24, 2000. Each of the above-identified application is hereby incorporated by reference.

STATEMENT REGARDING FEDERALLY SPONSORED RESEARCH

The work of this invention is supported in part by a grant from the Department of Energy. The United States Government has certain rights to this invention.

FIELD OF INVENTION

The present invention relates to the field of plant molecular biology. This invention concerns methods of regulating gene expression in transgenic plants. In particular, this invention discloses isolated and purified proteins which act as transcription factors capable of activating promoters to enhance gene expression.

DESCRIPTION OF RELATED ART

Bhattacharya—Pakrasi, et al., in. "Specificity of a promoter from a rice tungro bacilliform virus for expression in phloem tissues," *The Plant Journal,* 4(1):71-79 (1993) identified the promoter sequence in the rice tungro bacilliform virus (RTBV) genome. The article also reported that gene expression under the control of tie RTBV promoter occurred primarily in vascular bundles, particularly phloem and phloem associated cells in leaves.

Yin and Beachy, in "The regulatory regions of the rice tungro bacilliform virus promoter and interacting nuclear factors in rice (*Oryza sativa* L.)," *The Plant Journal,* 7(6) 969-980 (1995), described the E fragment (−164 to +45 in relation to the transcription start site) within the RTBV promoter which is sufficient to cause tissue-specific gene expression. The article also disclosed a critical cis element, Box II (−53 to −39), as a binding site for rice nuclear factor 2 (RNFG2) which is essential for promoter activity.

The same authors also identified other cis elements. Yin, et al., "Promoter elements required for phloem-specific give expression from the RTBV promoter in rice," *The Plant Journal:* 12(5): 1179-1188 (1997). These other cis elements are the ASL Box (−98 to −79) and a GATA motif (−143 to −135). Together, these cis elements (−164 to −32) conferred phloem-specific reporter gene expression. These regions act additively to direct tissue-specific expression.

Yin, et al., in "Rf2a, a bZIP transcriptional activator of the phloem-specific rice tungro bacilliform virus promoter, functions in vascular development," *The EMBO Journal,* 16, (17): 5247-5259 (1997), identifies a 1.8 kb transcription factor protein composed of 368 amino acids designated Rf2a. Rf2a binds to the Box II element and stimulates Box II—dependent transcription in vitro. When Rf2a protein accumulation is suppressed in transgenic plants, morphological changes—including stunted plants, twisted leaves which contain small disorganized vascular bundles, enlarged sclerenchyma and large intracellular air spores—appeared. The article teaches that the RTBV promoter interacts with a host transcription factor critical for leaf tissue differentiation and vascular development.

Beachy, in U.S. Pat. No. 5,824,857 entitled "Plant Promoter," describes the promoter from the rice tungro bacilliform virus (RTBV). The disclosure teaches that the RTBV promoter causes preferential expression in plant vascular tissue. The patent also teaches that the RTBV promoter can be used to drive expression in most plants, whether monocotyledonous or dicotyledonous, and is particularly suited to rice. The disclosure also teaches the transformation of plants by inserting the coding sequence of the promoter and a heterologous gene of interest to obtain transgenic plants which express the gene of interest in vascular tissue.

In plant biotechnology, selection of suitable promoters is crucial to obtaining expression of the gene of interest. Tissue specific promoters drive gene expression in a certain specific tissue or in several specific tissues of the plant. Constitutive promoters, on the other hand, drive gene expression in most tissues of a plant. While constitutive promoters are more widely used in the industry, tissue specific promoters are useful, or even necessary for some applications. A method of activating a tissue specific promoter to drive constitute gene expression thereby giving a greater degree of control over expression of the transgenes would be a valuable and useful tool to the industry.

Regulation of gene transcription is achieved by the activity of multiple transcription factors that bind to regulatory elements, many which are upstream of the promoters and alter basal rates of transcription initiation and/or elongation (1, 2). To understand the mechanisms of tissue-specific and constitutive gene expression in plants, a number of plant promoters and transcription factors have been studied in recent years (3-16). It was shown that constitutive promoters, such as the Cauliflower Mosaic Virus (CaMV) 35S promoter (17) and the promoter from Cassava Vein Mosaic Virus (CVMV) (14) have modular organizations, each of the multiple cis elements within the promoters confer cell type specific gene expression. These elements apparently interact in an additive and/or synergistic manner to control the gene expression pattern in all plant tissues. Similarly, tissue-specific promoters contain multiple elements that contribute to promoter activity in both positive and negative ways (4-6, 8, 12, 18). All these cis elements provide DNA targets for binding by transcription factors, the combinations of which contribute to regulation of gene expression controlled by the promoter.

The rice tungro bacilliform badnavirus (RTBV) promoter and the transcription factors that interact with this promoter serve as a model system to study plant tissue specific gene expression. RTBV is a plant pararetrovirus with a circular double-stranded DNA genome from which the pregenomic transcript is produced (19, 20). The virus, which replicates solely in phloem tissues, has a single promoter that is active in transfected protoplasts and is phloem specific in transgenic rice plants (7, 10, 21, 22).

Within the fragment E of the promoter (nucleotides −164 to +45), multiple cis elements were identified as being required for phloem specific gene expression and promoter activation (7, 10, 15, 23). A bZIP type transcription factor isolated from rice plants—Rf2a—binds to Box II, a crucial cis element of the RTBV promoter. It was subsequently shown that Rf2a activates transcription from this promoter in a rice in vitro transcription system (10, 11, 15). Moreover, studies in transgenic rice plants suggested that Rf2a is involved in the development of vascular tissues (11).

With the advancement of plant biotechnology comes the need for strong activation systems to regulate gene expression in transgenic plants. Non-plant transcription factors present a solution, however, given the differences between plants, mammals, *Drosophila* and yeast (24), the efficiency of such non-plant transcription factors may be negatively affected. It is important to develop a plant-based transcriptional regulatory system in the whole plant level. Accordingly, this invention teaches a plant-based transcriptional regulatory system based on the interaction between the transcription factors Rf2a and Rf2b and the RTBV promoter.

BRIEF SUMMARY OF THE INVENTION

It is an object of this invention to provide transcription factors which activate the RTBV promoter such that the promoter causes constitutive expression of the genes under its control.

This invention identifies the transcription factors Rf2a and Rf2b. The invention also teaches the function of the RTBV promoter in transgenic tobacco plants and the interaction between the transcription factors and the promoter. Methods of regulating gene expression are also provided.

This invention describes Rf2a, a bZIP protein that binds to the Box II cis element of the RTBV promoter, and Rf2b, the putative partner for Rf2a. Rf2b is capable of forming a heterodimer with Rf2a. The bZIP domain of Rf2b shares 72% nucleiotide identity with Rf2a. At the amino acid level, the two proteins share 83% identity. Rf2b has two putative functional domains: an acidic domain at the N-terminus and a proline rich domain at the C-terminus. Rf2b can bind to Box II and the mutant Box IIml (where the CCCC sequence is modified to GCGC).

This invention also provides a method of activating the RTBV promoter in vivo by exposing it to transcription factors Rf2a and/or Rf2b. As used herein, the term "activate" or "activating" means to regulate such that enhanced or constitutive expression of those genes which are under the control of the promoter results. The method of "exposing" the RTBV promoter comprises cloning the RTBV promoter coding sequence into a plasmid, cloning the coding sequence for Rf2a or Rf2b into a plasmid expression vector containing a CaMV 35S promoter and a Nos terminator, and cloning the plasmid expression vector containing the CaMV 35S promoter and the Nos terminator and either Rf2a or Rf2b sequence into the plasmid. Target plant cells would then be transformed using techniques known to those skilled in the art. The transgenic plant cells would then be allowed to grow.

BRIEF DESCRIPTION OF THE DRAWINGS

B. Schematic representations of the Rf2a transcription factor and of the 3Δ mutant. The potential activation domains are indicated as P for proline rich; A for acidic region; and Q for glutamine rich region. The dimerization and DNA binding domain is indicated as bZIP (Yin et al., Embo J. 1997).

C. Diagram of the constructs used for *Agrobacterium* mediated transformation of tobacco (*N tabacum*). Uid A gene (GUS encoding gene) is driven either by the Full Length rice tungro bacilliform virus promoter (FL) or E fragment (−164 to +45). The genes encoding the rice transcription factor Rf2a and the 3Δ mutant are driven by the 35S promoter of CaMV.

FIG. 2: Histochemical localization of GUS in tissue from transgenic tobacco plants. A, C, E, L, K: plants containing either PE:GUS or PFL:GUS genes. B, D, F, H, J, L: plants containing either PE::GUS(+)P35S::Rf2a or PFL::GUS(+) P35S::Rf2a. The results shown are representative of those observed in the 15 independent transgenic plants developed for each gene construct. Results with PE::GUS and PFL::GUS constructs were identical, and the figure is compiled from both sets of transgenic plants. GUS activity is indicated in transgenic tissue by an indigo dye precipitate after staining with X-Gluc. A, B: tobacco seedlings; C, D; juvenile leaves; E, F: roots; G, H: leaf sections showing vascular tissues of the midrib and leaf lamina; 1,3: vascular tissue of the leaf midrib; K, L: cross section of lamina. (c, cotyledon; cr, cortex; e, epidermis; ex, external phloem; g, guard cell; ip, internal phloem; l, leaf, m, mesophyll; p, phloem; pm, palisade mesophyll; py, parenchyma; rt, root tip-rv, root vein; sm, spongy mesophyll; t, trichome; vb, vascular bundle; x, xylem.)

FIG. 4: Correlation between GUS activity and the amount of Rf2a determined by ELISA for transgenic $T_0$ plant lines that carry PE::GUS(+)P35S:Rf2a or PFL:GUS (+)P35S:: Rf2a.

FIG. 5: Electrophoretic mobility shift assay (EMSA) of Rf2a and the 3Δ mutant of Rf2a. Oligonucleotides containing the BoxIIml sequences (Yin et al., 1997a) were used as $^{32}$P-labeled probe or an unlabeled competitor in an EMSA with 500 ng of *E. coli* protein containing 3Δ protein or Rf2a. Unbound probe is located near the bottom of the gel. The band with the greatest mobility in lanes 1, 2, 4, and 5 indicated by x is presumed to result from binding with an uncharacterized protein that co-purifies with the target protein. Lane 1, protein prepared from *E. coli* without induction. Lane 2, reaction with extracts of *E. coli* that produce Rf2a. Lane 3, reaction with equimolar amounts of Rf2a and 3Δ plus 80× fold molar excess of unlabeled competitor probe relative to the labeled probe. Lane 4, reaction with equimolar amounts of Rf2a and 3Δ. Lane 5, reaction with 3Δ.

DETAILED DESCRIPTION OF THE INVENTION

Phloem specific expression of the RTBV promoter. RTBV is known to accumulate in phloem tissues in infected rice plants. Similarly, the full length RTBV promoter (FL) and the E fragment of the promoter are expressed only in phloem tissues in transgenic rice plants (7, 10, 22). Within the E fragment, there are several cis DNA sequence elements that are conserved among vascular tissues (10). Box II is a cis element that is responsible for the basal behavior of the promoter. Box II shares homology with cis elements from other phloem and xylem specific promoters (10). Data from 5' deletion analyses showed that as long as Box II cis element is retained, the promoter is expressed in phloem tissues, although activity of the promoter is much lower in the absence of Box II than when it is present. It is known that some plant promoters retain specific expression patterns in different plant species (20-31) while others do not (32,33).

Rf2a can activate the promoter in cell types other than phloem cells. As we reported previously, the RTBV promoter contains several important cis elements, such as Box II, that contribute to expression of the promoter in vascular tissues. Data from 5' deletion analyses showed that as long as the Box II cis element is retained, the promoter is expressed in phloem tissues, although activity of the promoter is much lower in the absence of Box II than when it was present (10). He et al (15) reported that when the element, which contains Box II, was deleted or mutated in the context of the E fragment, the promoter activity dropped to basal levels.

To better understand the interactions between Rf2a and the RTBV promoter, the following plasmids were constructed: pGA-FL::GUS, which contains the full length RTBV promoter and the uidA reporter gene, uidA; pGA-E::GUS, which contains the E fragment and the uidA reporter gene; and pET-Rf2a, which contains the coding sequence for Rf2a. To study the effects of co-expression of Rf2a and the RTBV promoter, co-expression plasmids were constructed whereby the fusion gene P35S::Rf2a (which contains the CaMV35S promoter, the coding sequence of Rf2a and a Nos terminator) was cloned into pGA-FL::GUS and pGAE::GUS. The resultant co-expression plasmids, each containing the Box II cis element, are pGA-FL::GUS/P35S::Rf2a and pGA-E::GUS/P35S::Rf2a.

When plant cells were transformed with the co-expression plasmid, the pattern of GUS activity in transgenic plants was constitutive rather than phloem specific. This is consistent with the known pattern of expression of the 35S promoter (17) and indicates that Rf2a is involved in regulating expression of the RTBV promoter.

Many factors can influence the activity of transcription factors in controlling expression of the promoter, including affinity of binding of transcription factor with the DNA element (35), the subcellular distribution of factors, post-transcriptional modifications of the factor (36), and synergistic interactions with other proteins (37-41). Furthermore, it is common to construct promoters by combining multiple upstream activation sequences and by replicating activation domains on DNA binding proteins. In the activation system we described here, a single copy of Box II together with Rf2a was sufficient to increase expression of the RTBV promoter. In addition, the level of expression was positively correlated with the level of Rf2a. Other reports indicate that expression of P-35S::GUS fusion genes in taansgenic plants range from 321 U (IU is equivalent to pmol 4-MU $min^{-1}$ $mg^{-1}$) to 113,000 U (17, 27, 42, 43). In our studies transgenic tobacco plants had GUS activity between 4,000 U and 18,000 U when P-FL::GUS or P-E::GUS were activated by expression of the P35S::Rf2a enhancer gene, representing a 2 to 20 fold activation of the reporter gene.

Although we do not yet know the basis for the strong activation of the FL and E promoters by Rf2a, there are several notable characteristics of this system. First, Rf2a binds to a cis element (Box II) that is located very close to the TATA box (within approximately 7 nt). It is not yet known if proximity of the cis element to the TATA sequence is important for the activity of Rf2a in expressing this promoter. Second, the results of in vitro studies indicate that there is a direct physical interaction between TATA Binding Protein (TBP), and Rf2a (Q. Zhu et al., in preparation). Third, Rf2a has three putative activation domains: acidic, glutamine rich, and proline rich domains (11), any or all of which may be important for the activity of Rf2a. We propose that proximity of the cis element and the unique features of Rf2a contribute to the strong activation of the promoter by Rf2a.

In transgenic plants in which the reporter genes are activated by the gene P35S::Rf2a, it is most likely that promoter activation is due to formation of homodimers of Rf2a. However, the activation by heterodimerization of Rf2a with homologous factors in tobacco cannot be completely excluded. The observation that E fragment and FL promoters are expressed in phloem tissues in tobacco plants suggests that there is/are Rf2a-like transcription factor(s) in tobacco.

A dominant negative mutant of Rf2a affects plant development. In rice plants, Rf2a acts as a transcription activator and its biological function is linked to the development of the vascular system: this conclusion was based upon the results of experiments with transgenic rice plants in which the levels of Rf2a were reduced by an anti-sense approach (11). An alternative approach to determine gene function is to use directed mutagenesis of Rf2a and determine the effects of mutations on the function of genes that require the activity of Rf2a and proteins that form heterodimers with Rf2a. Mutants of bZIP transcription factors have been used in such studies and found to act as dominant negative mutants (44-46). Here, the mutant 3Δ, which contains only the DNA binding domain and the leucine zipper region, was created to test the biological function of Rf2a-like transcription factors in tobacco, and the effect of 3Δ on expression of the RTBV promoter. This study, showed that the 3Δ mutant is capable of forming homodimers. The 3Δ mutant also formed heterodimers with Rf2a. Both dimers bind to Box II in vitro.

The invention is exemplified by the following non-limiting example.

EXAMPLE 1

Figure 1:
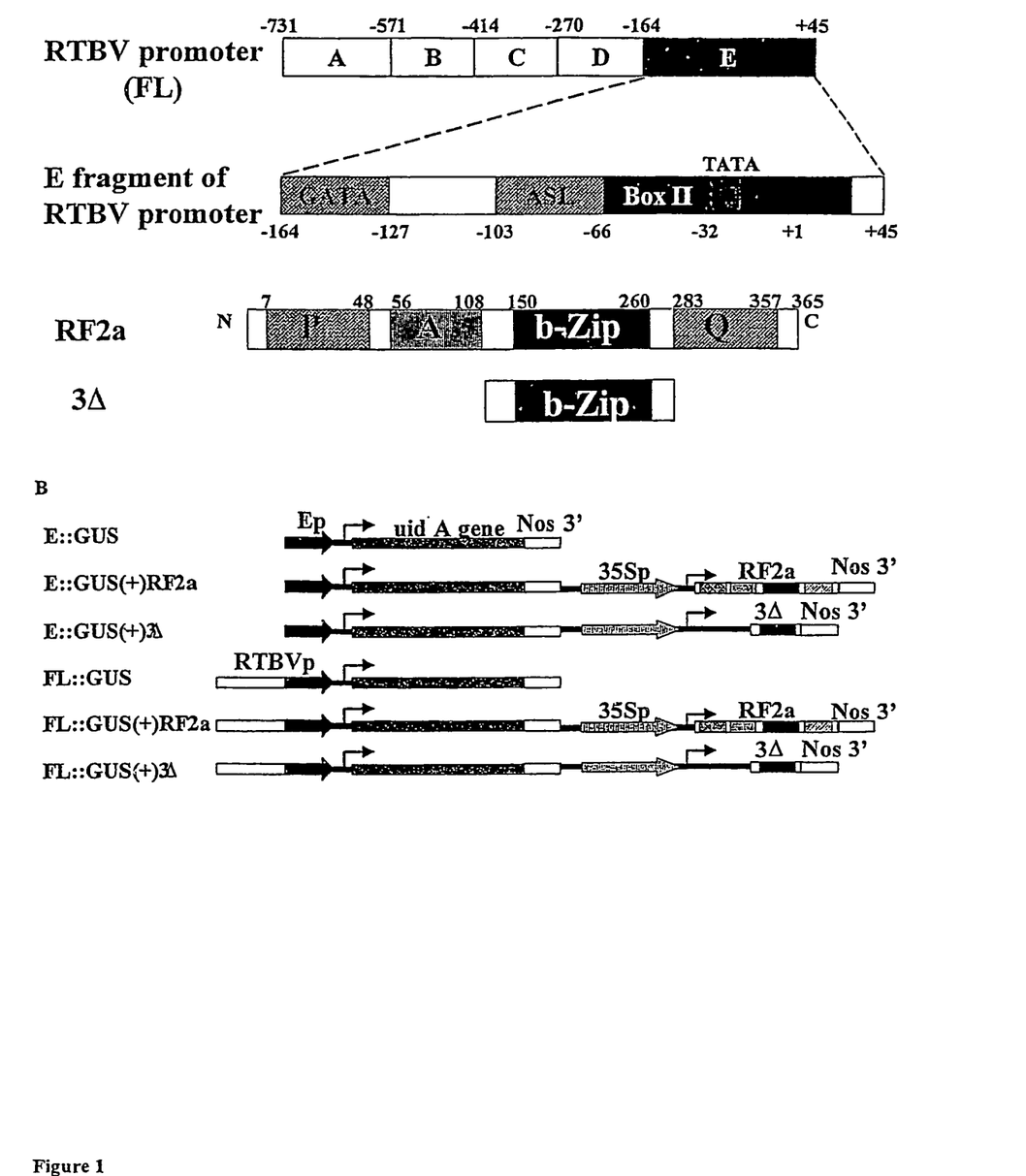
FIG. 1: A: Schematic representation of the RTBV full-length promoter (FL) and of the E fragment (E) of the promoter. The cis elements GATA, ASL, Box II and Box I of E (described by Yin et al., Plant J. 1997) are indicated. Box II, the cis element to which Rf2a binds, is indicated in black.

Expression pattern of the RTBV promoter in transgenic tobacco plants. The RTBV full length (FL) promoter containing nucleotides −731 to +45 of the RTBV genome, is expressed exclusively in phloem tissues in transgenic rice plants (7, 10, 22). A fragment of the RTBV promoter, termed the E fragment and comprising nucleotides −164 to +45, is also expressed exclusively in phloem tissues (7). Within the E fragment four cis sequence elements that contribute to phloem specific gene expression have been described, including the GATA motif, ASL (AS-1 like) element, Box II and Box I sequence elements (as shown in FIG. 1A) (10). Since the host range of RTBV is limited to rice, we wished to determine whether the RTBV promoter is functional and maintains tissue specificity in transgenic tobacco plants. The RTBV promoter FL and the E fragment were ligated with the uid A coding sequence to produce the chimeric genes P-FL::GUS and P-E::GUS. The genes were ligated to a $T_1$, plasmid vector (as shown in FIG. 1A) and introduced into tobacco through *Agrobacterium*-mediated transformation. 17 and 23 independent transgenic tobacco plants were developed for the P-FL::GUS and P-E::GUS constructs, respectively.

Figure 2:
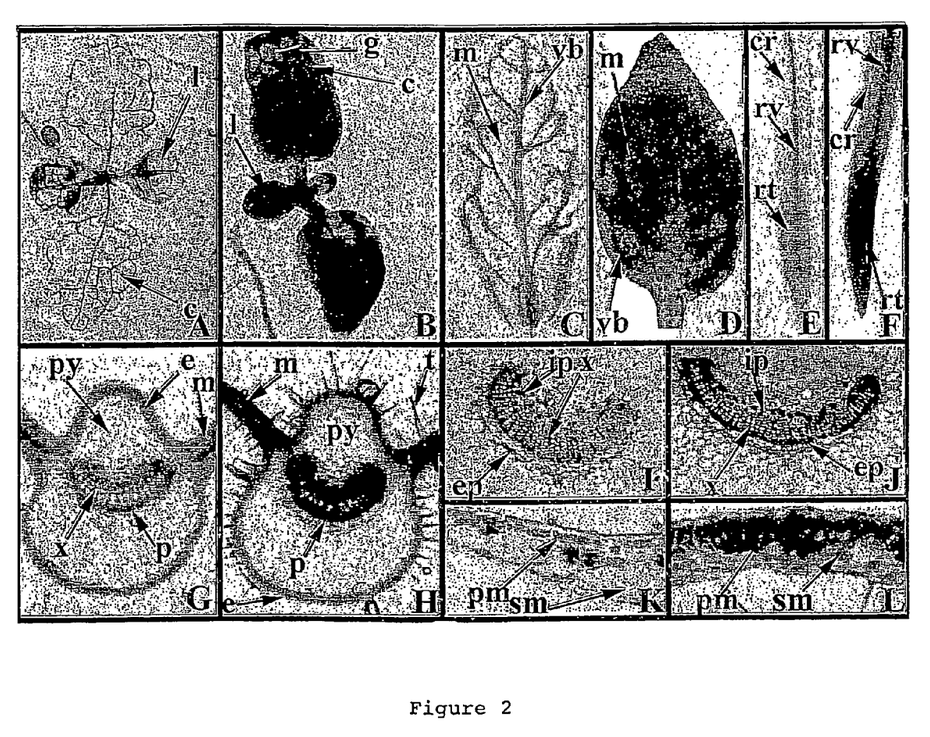

A detailed histochemical analysis of GUS expression patterns in taansgenic tobacco plants showed that expression of P-E::GUS and P-FL::GUS were essentially the same (as shown in FIG. 2). In leaves of transgenic plants with P-E::GUS, strong GUS activity was observed in vascular tissues (as shown in FIG. 2A, C) although in very young leaves there was a low amount of GUS activity in mesophyll cells (as shown in FIG. 2A). Cross sections through the midrib of more mature leaves showed GUS activity only in phloem cells (as shown in FIG. 2 G). These results are similar to those reported from studies of transgenic rice plants (10).

Modulation of phloem specific expression of the RTBV promoter by Rf2a. Rf2a, was isolated by virtue of its interaction with Box II DNA (10); a cDNA encoding Rf2a was subsequently isolated and characterized. Rf2a is a bZIP protein with three potential functional domains: a proline-rich domain, an acidic domain and a glutamine-rich domain (as shown in FIG. 1A) (11). A mutant of Rf2a that lacks these three putative functional domains was constructed and is referred to as "3Δ" (as shown in FIG. 1A, B). The $^3A$ protein contains the DNA binding and leucine-zipper domains (bZIP) of Rf2a, including the putative nuclear localization signal. To determine the regulatory functions of Rf2a and $^3A$ mutant on expression of the FL and E fragment promoters in transgenic tobacco plants, the following $T_1$, binary plasmids were constructed: PGA-E::GUS/P-35S::Rf: 2a, pGA-E::GUS/P-35S::3Δ, pGA-FL::GUS/P-35S::RF2A, pGA-FL::GUS/P-35S::3Δ (as shown in FIG. 1B). At least 15 independent transgenic tobacco lines with each construct were developed through *Agrobacterium*-mediated transformation. The integration of the full-length T-DNA in transgenic plants was confirmed by Southern blot hybridization analysis (data not shown).

Histochemical analysis of GUS activity in the TI progeny showed that expression of the reporter genes was substantially altered by co-expression of Rf2a. In the plants that contained either P-E::GUS/P-35S::Rf2a or P-FL::GUS/P-35S::Rf2a, GUS activity was detected throughout the cotyledonary leaves (as shown in FIG. 2B) and true leaves (as shown in FIG. 2C). Cross sections through the leaf midrib of these plants showed very strong GUS activity in phloem cells, the epidermis and trichomes (Compare G and H in FIG. 2). The palisade and spongy mesophyll cells of the leaf lamina also exhibited intense staining (compare FIGS. 2L and K) as did parenchyma cells of the midrib (compare I and J in FIG. 2). Guard cells showed strong GUS activity when the FL::GUS gene was co-transformed with P-35S::R-F2a (not shown). In the root tissues of transgenic plants that contained P-3::GUS/P-35S::Rf2a or P-FL::GUS/P35S:: Rf2a, there was a high level GUS activity throughout the cortex (as shown in FIG. 2F), and very strong levels of GUS activity in root tips. In contrast, root tissues of transgenic plants that were transformed only with reporter genes revealed GUS activity only in the vascular cylinder (as shown in FIG. 2E).

Figure 3:
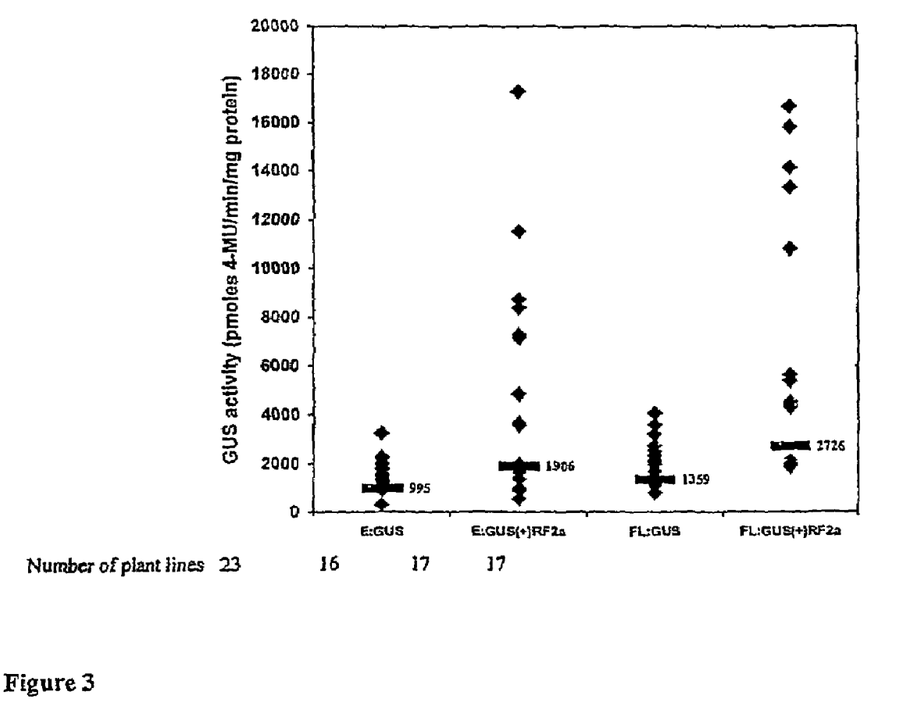
FIG. 3: GUS activity in extracts of leaves from Ro transgenic tobacco plants carrying the PE::GUS gene, PE:: GUS(+)P35S:Rf2a, PFL::GUS or PFL:GUS (+)P35S::Rf2a. The amount of GUS (pmoles 4–MU min$^{-1}$ mg$^{-1}$ protein) is indicated. The mean level of GUS activity for each construct is indicated by the thick, horizontal bar.

GUS activity in the leaves of $T_O$ transgenic tobacco plants was quantified using MUG in a fluorescence assay. As anticipated, there were variations in the amount of GUS activity among transgenic lines for each construct. The GUS activity of transgenic plants with P-FL::GUS was higher than the activity in plants with P-E::GUS genes (as shown in FIG. 3) When Rf2a was co-expressed with either P-E::GUS or PFL::GUS, the GUS activity was increased by 2 to 20 fold compared with plants that lacked Rf2a (as shown in FIG. 3). The increase of GUS activity is in agreement with the observation that the pattern of GUS activity was constitutive when Rf2a was co-expressed with the reporter gene (as shown in FIG. 2).

Figure 4:
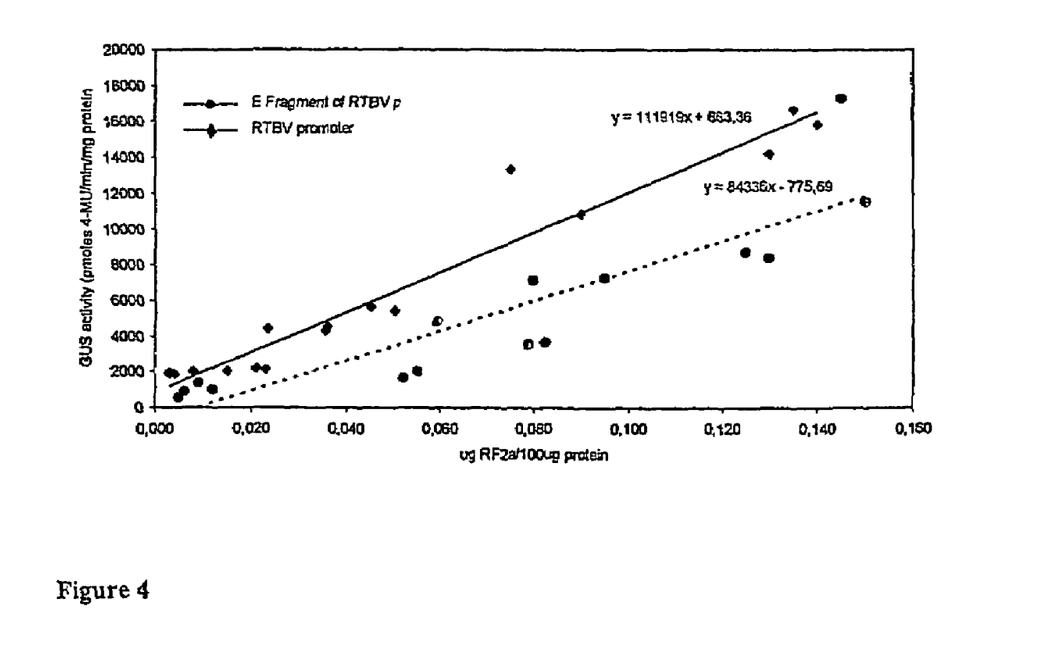

To establish a correlation between the GUS activity and the amount of Rf2a, ELISA reactions were carried out to quantitatively measure the amount of Rf2a in individual transgenic plants. Soluble protein samples of To plants were triturated and aliquots of soluble proteins were tested in quantitative ELISA reactions using anti-Rf2a antibodies. Aliquots of the same set of extracts were also used in quantitative analyses of GUS activity. As shown in FIG. 4, the results of these assays showed a positive correlation between the amount of Rf2a in the samples and GUS activity.

Figure 5:
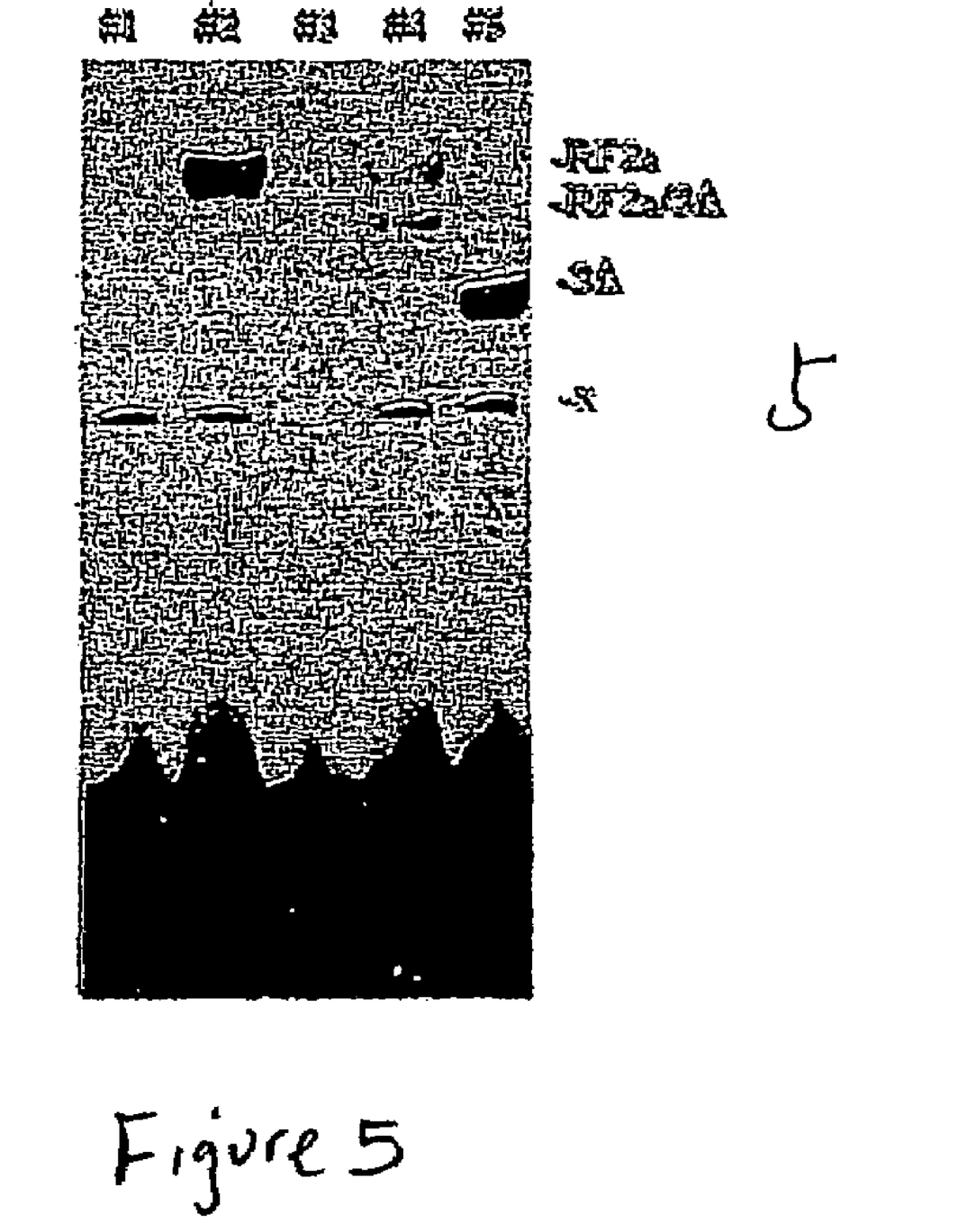

DNA binding and heterodimerization of Rf2a and 3Δ. The gene encoding the mutant protein 3Δ, which lacks the three putative regulatory domains of Rf2a, was constructed to determine if it can restrict expression of the RTBV promoter. It has been reported that sequences outside of the leucine zipper region of such proteins can contribute to dimer stabilization (28). In these cases deletions of other (putative) domains can affect the ability of the protein to form homo—or heterodimers, and to bind DNA. To test the DNA binding ability of mutant protein 3Δ, EMSAs were carried out (as shown in FIG. 5). Rf2a and 3Δ can each bind 32P-labeled BoxIIml, presumably by forming homodimers (lanes 2 and 5). When both proteins are added, a band with mobility intermediate with the mobilities of the probe to which Rf2a and 3Δ homodimers are bound was observed. This band is presumed to correspond to the binding of the heterodimer $Rf^2a/3Δ$ with the probe (lane 4). All of these complexes can be competed by 80× molar excess of unlabeled cold probe (lane 3).

Figure 6:
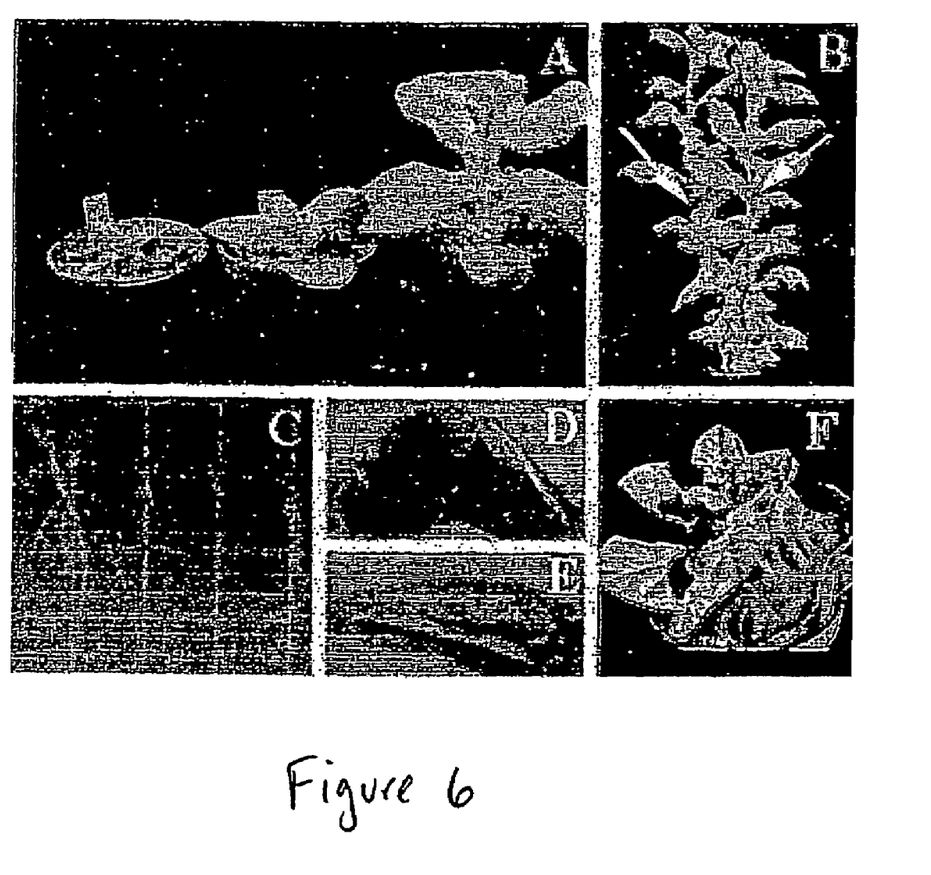
FIG. 6: Phenotypes of plants that contain the gene encoding the 3Δ mutant of Rf2a A, C, segregation of the stunting phenotype with the transgene. A: the plants on the left contain the transgene and grew more slowly than the plant that lacked the transgene due to segregation in the $T_1$ generation (right). C: size of roots in plants with the 3Δ gene (plants on the right) compared with non-transgenic $T_1$ progeny (left). B: intermediate phenotype, showing shoot elongation, curvature of leaves and decreased apical dominance. D, E: close up of leaves showing downward curvature. F: abnormal plant showing the phenotype of severe stunting with thick leaf lamina.
Figure 7:
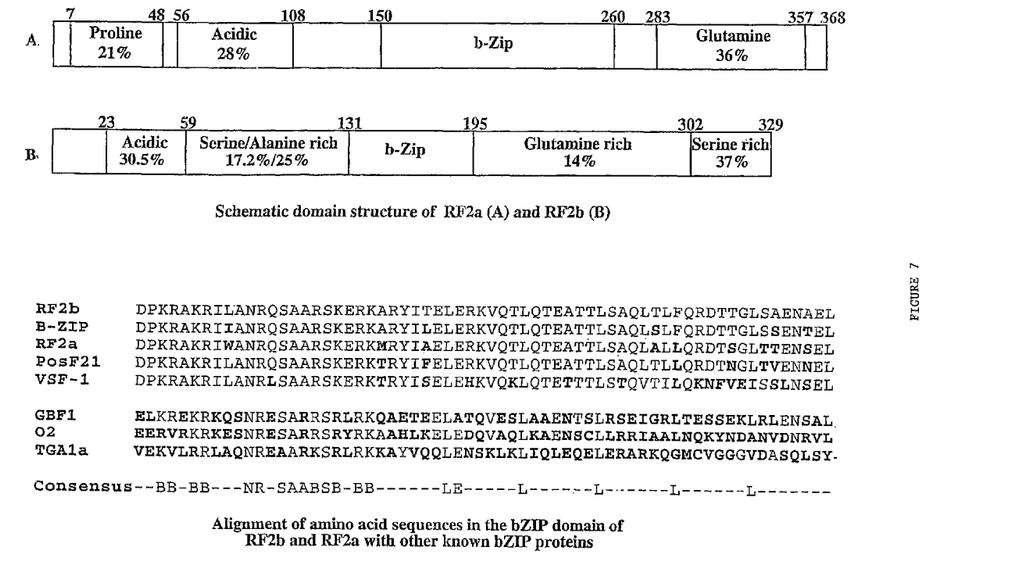
FIG. 7: A schematic diagram of the domain structures of Rf2a and Rf2b, and an alignment of amino acid sequences in the bZIP domain of Rf2a and Rf2b with other known bZIP proteins (piece of SEQ ID NO: 2, SEQ ID NO: 7, piece SEQ ID NO: 1, SEQ ID NO: 8, SEQ ID NO: 9, SEQ ID NO: 10, SEQ ID NO: 11 and SEQ ID NO: 12, respectively, in order of appearance, from top to bottom).

Morphological changes of transgenic plants with 3Δ. A gene encoding $^3A$ protein was introduced along with the reporter gene into tobacco (FIG. 1B), and 15 independent lines carrying either the P-E::GUS/P-355::3Δ or the P-FL:: GUS/P-35S::3Δ genes were developed. Of these, 7 lines carrying the P-E::GUS/P-35S::3Δ genes, and 6 lines carrying the P-FL::GUS/P35S::3Δ genes exhibited abnormal phenotypes. In contrast, no abnormal phenotypes were observed in transgenic lines with reporter gene constructs alone, or reporter genes plus the Rf2a gene. The abnormal $T_o$ transgenic lines carrying P-E::GUS/P-35S::3Δ or P-FL::GUS/P-35S::3Δ genes were characterized by downward curving of the mid-vein (FIGS. 6D,E,F), and the most severely affected plants were stunted (as shown in FIG. 6A). Two of the affected plants exhibited abnormal floral development: these lines did not produce seeds To confirm that the abnormal phenotypes were due to the transgene, we analyzed the $T_1$, generation of the abnormal plant lines that gave seeds. Among all of the 11 lines tested, the abnormal phenotype was inherited through the second generation. Line 1 of plants carrying P-FL::GUS/P-35S::3Δ showed an abnormal segregation pattern, while the segregation of phenotype in other lines, for the most part, followed classical, single locus segregation patterns. Abnormal plants grew much more slowly than the normal plants in $T_1$ progeny, and were characterized by stunting of shoots and roots (as shown in FIGS. 6A, Q). The abnormal phenotype of $T_1$ plants that contained the P-E::GUS/P-35S::3Δ and P-FL::GUS/P-35S::3Δ genes can be characterized as either mild (as shown in FIG. 6B) or severe (as shown in FIG. 6F). Plants with the mild phenotype grew much more slowly than non-transgenic control plants but they ultimately achieved normal height. These plants had wrinkled or distorted leaves (as shown in FIGS. 6D, E) with yellow and green mosaic leaf color and exhibited reduced apical dominance and the appearance of lateral shoots (as shown in FIG. 6B, see arrows). Plants that exhibited a severe phenotype were stunted with very short internodes, thick leaf lamina, and an increased number of side shoots (as shown in FIG. 6F). The developmental problems in plants were severe and the plants did not produce fertile flowers.

Expression of the 3Δ gene in the $T_1$ progeny was confirmed by northern blot analysis (data not shown). There was no correlation between severity of the abnormal phenotype and the accumulation of mRNA derived from the transgene.

GUS activity of transgenic lines with the P-E::GUS/P-35S::3Δ or P-FL::GUS/P-35S::3Δ genes were analyzed. The transgenic lines that did not show an abnormal phenotype had the same levels of GUS activity as the lines that contained only the reporter gene (i.e. P-E::GUS or P-FL::GUS) and there was no clear indication of gene activation or repression. Some of the lines that exhibited abnormal morphology (i.e., lines j, n, o of P-E::GUS/P35S::3Δ; lines e, h, k of PFL::GUS/P-35S::3Δ) had a similar level of GUS activity as transgenic lines that contained only the reporter genes. No correlation was established between severity of plant phenotype and GUS activity. In some lines with severely abnormal phenotypes, GUS activity increased with the age of the plants. These plants were physiologically different from normal plants and we suggest that factors other than those related to the 3& mutant protein may affect expression of the RTBV promoter in these plants.

METHODS

Plasmid constructions. The complete RTBV promoter (nucleotides—731 to 45) ligated with the uida coding sequence was released from plasmid pMB9089 (7) by digestion with XbaI and KpnI. The chimeric gene comprising the E fragment of the RTBV promoter (nucleotides—164 to +45) and the uidA coding sequence was released from plasmid pMB9089 (7) by digestion with Hind III and Kpn I. Inserts were purified and ligated into the binary vector pGA482 through XBA I and Kpn I or Hind III and Kpn I sites. The resultant plasmids are named pGA-FL::GUS and pGAE::GUS, respectively (as shown in FIG. 1B).

To construct plasmids for in vitro expression of Rf2a and the bZIP DNA binding domain of Rf2a (referred to as 3Δ) (as shown in FIG. 1A) the plasmid pET-12a, which contains the cDNA encoding Rf2a, (11) was used. The Rt2a coding sequence was amplified by PCR from the starting plasmid by using primers 5'Rf2a (GCCGCC CATATGGAGAAGATGAACAGGGAGAAATCC) (SEQ ID NO: 3) and 3'Rf2a (CG CGGATCCTCAGTTGCCGCTGCTTCCTGA) (SEQ ID NO: 4). NdeI and BamHI sites were introduced into the 5'and 3'primers, respectively (underlined). The coding sequence for 3Δ,comprising amino acids 108 to 283 of Rf2a (11), was amplified by PCR from the Rf2a cDNA by using primers 5'ΔPΔQΔA-Rf2a (GCCGCC CATATGGAGAAGATGTCCGCCGCCGCCCA) (SEQ ID NO: 5) and 3'Δ-Rf2a (CG CGGATCCTCAGTGTGGCATGCCACCGAA) (SEQ ID NO: 6). As described above, Nde I and Bam HI sites were introduced into the primers. Pfu DNA polymerase (Stratagene) was used in all PCR reactions. The PCR products were digested with Nde I and Bam HI and inserted into pET28a (Novagen) restricted by the same enzymes. The new constructs were named pET-Rf2a and pET-3ΔThe sequence of inserts in each plasmid was confirmed by DNA sequencing.

Plant transformation vectors for co-expression of the reporter gene and the effector proteins were constructed. The coding sequences of Rf2a and 3Δ insert were released from pET-Rf2a and pET-3Δ with Nde I and Bam HI. The DNA fragments were then cloned into the plant expression vector pMON999 (a gift from Monsanto Co.), which contains the CaMV 35S promoter (P35S) and Nos terminator, after the plasmid was restricted by Xba I (blunted with Klenow plus dNTPs) and Barn HI. The fusion genes named P35S::Rf2a or P35S::3Δ were released by NotI and blunted with Klenow4 polymerase plus dNTPs. The two fusion genes were then cloned into binary vectors pGA-E::GUS or pGAFL::GUS through the blunted ClaI site. In the co-expression vectors, the reporter gene and effector genes are in head to tail orientation. The final plasmids were named pGA-E::GUS/P35S::Rf2a, pGA-FL::GUS/P-35S::Rf2a, PGAE::/GUS/P-35S::3Δ and pGA-FL::GUS/35S.3Δ (as shown in FIG. 1B).

Tobacco transformation. Gene constructs containing pGA482 derived plasmids (as shown in FIG. 1B) were introduced into *Agrobacterium tumefaciens* strain LBA4404 by electroporation and used for *Agrobacterium*-mediated transformation. Leaf discs from *Nicotiana tabacum* cv. Xanthi NN were used for transformation following the protocol described by Horsch et al (25). At least 14 independent transgenic lines for each construct were produced and grown in a greenhouse. The transgenic plants were self-fertilized and $T_1$ seeds were collected. For the analysis of the $T_1$ generation, seeds were germinated on Murashige and Skoog (MS) medium (26) with or without kanamycin (100 mg/l) selection and the seedlings were grown in a greenhouse.

Analysis of GUS activity. Histochemical analysis of B-glucuronidase (GUS) activity was performed essentially as described by Jefferson et al (27). Hand-cut fresh tissue sections of leaves and stems of primary transformants $T_0$ or $T_1$, progeny were incubated at 37° C. for 4 to 12 hours in reaction buffer containing 1 mM 5-bromo4-chloro-3-indolyl glucuronide (X-gluc) (Research Organic), 100 mM sodium phosphate buffer pH 7, 2 mM potassium ferrocyanide and potassium ferricyanide, 0.1% Triton X-100 and 20% methanol. For analysis of young $T_1$ seedlings, whole platelets were collected about one week after germination and immersed in the buffer containing X-gluc. After vacuum infiltration, incubation was carried out overnight at 37° C. Samples were cleared by several washes with 70% ethanol. Stained sections were immersed in 75% glycerol and visualized by optical microscopy.

Quantitative GUS analyses using the substrate 4, methylumebelliferone-β-S glucuronide (MUG) were performed as described by Jefferson et al. (27).

ELISA. To detect Rf2a in extracts of transgenic tobacco leaves, sandwich ELISAs were performed. 96-well microfilter plates (Nunc, MaxiSorp) were coated overnight at 4°

C. with Protein A at 1 ug/ml in PBS, 100 ul/well (Pierce). Plates were incubated for 1 hour at room temperature in blocking buffer [1×PBS containing 10% (v/v) Fetal Bovine Serum. (FBS)]. Plates were incubated with the purified anti-Rf2a antibody (7) at 1 ug/ml in 1×PBS plus 1% (v/v) FBS, for 1 hour at room temperature. Plant extracts in 50 mM Tris-HCl, pH 7.5, 0.1% v/v) Triton×100 were added and the plates were incubated overnight at 4° C. Residual protein A binding sites were blocked with protein A at 1 ug/ml in 1×PBS plus 1% (v/v) FBS. Plates were incubated again with the purified anti-Rf2a antibody, 1 ug/ml in 1×PBS plus 1% (v/v) FBS, for 1 hour at room temperature, and then with protein-A-HRP (Pierce) at 1 ug/ml in 1×PBS plus 1% (v/v) FBS and developed with TMB (KPL, Maryland, USA). Plates were read at 650 nm with an absorbency plate reader. Between each incubation step, five washes with 1×PBS were performed. Purified Rf2a was used to create a standard curve to quantify the amount of Rf2a in each sample.

Production of Rf2a and pET-3Δ in *E. coli*, pET-Rf2a and pET-3Δ were transformed into *E. coli* BL21 (DE3)/pLysE. Cells were grown at 37° C. to an $OD_{600}$ of 0.5-0.6, induced by 0.5 mM isopropyl-β-D-thiogalactopyranoside (IPTG) for 3 h at 250C. The cell pellets were resuspended in 20 mM Tris-HCl pH 8, 500 mM NaCl, 0.1% NP40, 1 mM PMSF, 1 mg/ml lysozyme, 10 ug/ml DNAase and 10 ug/ml RNase. Lysis was completed using a French press. Under these conditions the target proteins were soluble, and were dialyzed against Silvana and stored at −80° C.

Electrophoretic mobility shift assays (EMSAs). EMSAs were carried out essentially as described by Yin and Beachy (7). 500 ng of *E. coli* protein extracts were incubated with $32_P$ labeled DNA probes comprising Box IIml that was constructed using annealed oligonucleotides (10). For competition EMSA, unlabeled oligonucleotides were added to the binding reactions at 80 fold molar excess relative to the labeled probe (see FIG. 5).

REFERENCES

The following references are incorporated by reference.
1. Roeder, R. G. (1991) *Trends Biochem Sci* 16, 402-8.
2. Yankulov, K., Blau, J., Purton, T., Roberts, S. & Bentley, D. L. (1994) *Cell* 77, 749-59.
3. Benfey, P. N. & Chua, N.-H. (1989) *Science* 244, 174-181.
4. Leyva, A., Liang, X., Pintor-Toro, J. A., Dixon, R. A. & Lamb, C. J. (1992) *Plant Cell* 4, 263-71.
5. Fujiwara, T. & Beachy, R. N. (1994) *Plant Mol Biol* 24, 261-72.
6. Suzuki, M., Koide, Y., Hattori, T., Nakamura, K. & Asahi, T. (1995) *Plant Cell Physiol* 36, 1067-74.
7. Yin, Y. & Beachy, R. N. (1995) *Plant J* 7, 969-80.
8. Ellerstrom, M., Stalberg, K., Ezcurra, I. & Rask, L. (1996) *Plant Mol Biol* 32, 1019-27.
9. Faktor, O., Kooter, J. M., Dixon, R. A. & Lamb, C. J. (1996) *Plant Mol Biol* 32, 849-59.
10. Yin, Y., Chen, L. & Beachy, R. (1997) *Plant J* 12, 1179-88.
11. Yin, Y., Zhu, Q., Dai, S., Lamb, C. & Beachy, R. N. (1997) *Enbo J* 16, 5247-59.
12. Ringli, C. & Keller, B. (1998) *Plant Mol Biol* 37, 977-88.
13. Verdaguer, B., de Kochlko, A., Beachy, R. N. & Fauquet, C. (1996) *Plant Mol Biol* 31, 1129-39.
14. Verdaguer, B., de Kochko, A., Fux, C. I., Beachy, R. N. & Fauquet, C. (1998) *Plant Mol Biol* 37, 1055-67.
15. He, X., Hohn, T. & Futterer, J. (2000) *J Biol Chem* 275, 11799-808.
16. Niggeweg, R, Thurow, C., Weigel, R., Pfitzner, u. & Gatz, C. (2000) *Plant Mol Biol* 42, 775-88.
17. Benfey, P. N., Ren, L. & Chua, N.-H. (1989) *The EMBO J* 8, 2195-2202.
18. Hauffe, K. D., Lee, S. P., Subramaniam, R. & Douglas, C. J. (1993) *Plant J* 4, 235-53.
19. Qu, R. D., Bhattacharyya, M., Laco, G. S., De Kochko, A., Rao, B. L., Kaniewska, M. B., Elmer, J. S., Rochester, D. E., Smith, C. E. & Beachy, R. N. (1991) *Virology* 185, 354-64.
20. Hay, J. M., Jones, M. C., Blakebrough, M. L., Dasgupta, I., Davies, J. W. & Hun, R. (1991) *Nucleic Acids Res* 19, 2615-21.
21. Chen, G., Muller, M., Potrykus, I., Hohn, T. & Futterer, J. (1994) *Virology* 204, 9-100.
22. Kloti, A., Henich, C., Bieri, S., He, X., Chen, G., Burkhardt, P. K., Wunn, J., Lucca, P., Hohn, T., Potrykus, I. & Futterer, J. (1999) *Plant Mol Biol* 40, 249-66.
23. Meisel, L. & Lam, E. (1997) *Genet Eng* 19, 183-99.
24. Horsch, R. B., Fry, J., Hoffmann, N., Neidermeyer, J., Rogers, S. G. & Fraley, R. T. (1988) in *Plant Molecular Biology Manual*, eds. Gelvin, S. B. & Schilperoort, R. A. (Kluwer Academic Publishers, Dordrecht, Netherlands), pp. A5/1-9.
25. Murashige, T. & Skoog, F. (1962) *Phlysiol. Plant* 15, 473-497.
26. Jefferson, R. A., Kavanagh, T. A. & Bevan, M. W. (1987) *Embo J* 6, 3901-7, 28.
27. Katagiri, F., Seipel, K & Chua, N. H. (1992) *Mol Cell Biol* 12, 4809-16, 29.
28. Medberry, S. L. & Olszewski, N. E. (1993) *Plant J* 3, 619-2.6.
29. Torbert, K. A., Gopalraj M., Medberry, S. L., Olszewski, N. E. & Somers D. A. (1998) *Plant Cell Reports* 17, 284-287.
30. John, M. & Petersen, M. (1994) *Plant Mol Biol* 26, 1989-93.
31. Diaz, I., Royo, J., O'Connor, A. & Carbonero, P. (1995) *Mol Gen Genet* 248, 592-8.
32. Gallusci, P., Salamini, F. & Thompson, R. D. (1994) *Mol Gen Genet* 244, 391400.
33. Medberry, S. L., Lockhart, B. E. & Olszewski, N. E. (1992) *Plant Cell* 4, 185-92.
34. Giniger, E., Varnum, S. M. & Ptashne, M. (1985) *Cell* 40, 767-74.
35. Roberts, S. G. & Green, M. R. (1995) *Nature* 375, 105-6.
36. Lin, Y. S., Carey, M., Ptashne, M. & Green, M. R (1990) *Nature* 345, 359-61.
37. Carey, M., Lin, Y. S., Green, M. R. & Ptashne, M. (1990) *Nature* 345, 3614.
38. Emami, K. H. & Carey, M. (1992) *Embo J* 11, 5005-12.
39. Ohashi, Y., Brickman, J. M., Furman, E., Middleton, B. & Carey, M. (1994) *Mol Cell Biol* 14, 2731-9.
40. Schwechheimer, C., Smith, C. & Bevan, M. W. (1998) *Plant Mol Biol* 36, 195-204.
41. Sanger, M., Daubert, S. & Goodman, R. M. (1990) *Plant Mol Biol* 14, 433-43.
42. Weinmann, P., Gossen, M., Hillen, W., Bujard, H. & Gatz, C. (1994) *Plant J* 5, 559-69.
43. Eckardt, N. A., McHenry, L. & Guiltinan, M. J. (1998) *Plant Mol Biol* 38, 539-49.
44. Fukazawa, J., Sakai, T., Ishida, S., Yamaguchi, I., Kamiya, Y. & Takahashi, Y. (2000) *Plant Cell* 12, 901-15.
45. Miao, z. H. & Lam, E. (1995) *Plant J* 7, 887-96.
46. Qin, x. F., Holuigue, L., Horvath, D. M. & Chua, N. H. (1994) *Plant Cell* 6, 863-74.

47. Ulmasov, T., Hagen, G. & Guilfoyle, T. (1994) *Plant Mol Biol* 26, 1055-64.
48. Pascuzzi, P., Hamilton, D., Bodily, K. & Arias, J. (1998) *J Biol Chem* 273, 26631-7.
49. Amaya, E., Musci, T. J. & Kirschner, M. W. (1991) *Cell* 66, 257-70.
50. Ransone, L. J., Visvader, J., Wamsley, P. & Verma, I. M. (1990) *Proc Natl, Acad Sci USA* 87, 3806-10.
51. Inukai, T., Inaba, T., Yoshihara, T. & Look, A. T. (1997) *Mol Cell Biol* 17, 1417-24.

TABLE 1

Segregation of the abnormal phenotype in the R1 generation

| Construct | Abnormal Morphology/Total Plant Lines in the R0 | Line | Morphology Abnormal | Normal |
|---|---|---|---|---|
| E::GUS (+) 3Δ | 7/15 | i | 7 | 3 |
| | | k | 16 | 4 |
| | | l | 5 | 5 |
| | | m | 5 | 0 |
| | | n | 7 | 3 |
| | | o | 10 | 12 |
| FL::GUS (+) 3Δ | 6/15 | e | 7 | 3 |
| | | h | 7 | 3 |
| | | k | 14 | 7 |
| | | l | 2 | 8 |
| | | n | 8 | 1 |

Predicted amino acid sequence of RF2a

```
MNREKSPIPG DGGDGLPPQA TRRAGPPAAA AAAEYDISRM
PDFPTRNPGH RRAHSEILSL PEDLDLCAAG GGDGPSLSDE
NDEELFSMFL DVEKLNSTCG ASSEAEAESS SAAAHGARPK
HQHSLSMDES MSIKAEELVG ASPGTEGMSS AEAKKAVSAV
KLAELALVDP KRAKRIWANR QSAARSKERK MRYIAELERK
VQTLQTEATT LSAQLALLQR DTSGLTTENS ELKLRLQTME
QQVHLQDALN DTLKSEVQRL KVATGQMANG GGMMMNFGGM
PHQFGGNQQN FQNNQAMQSM LAAHQLQQLQ LHPQAQQQQV
LHPQHQQQQP LHPLQAQQLQ QAARDLKMKS PMGGQSQWGD
GKSGSSGN
```

Predicted amino acid sequence of RF2b (SEQ ID NO: 2)

```
MQEPKHTDPA AMRGAHHRRA RSEVAFRLPD DLDLGGGGAG
AFDEIGSEDD LFSTFMDIEK ISSGPAAAGG SDRDRAAETS
SPPRPKHRHS SSVDGSGFFA AARKDAAASL AEVMEAKKAM
TPEQLSDLAA IDPKRAKRIL ANRQSAARSK ERKARYITEL
ERKVQTLQTE ATTLSAQLTL FQRDTTGLSA ENAELKIRLQ
AMEQQAQLRD ALNDALKQEL ERLKLATGEM TNSNETYSMG
LQHVPYNTPF FPLAQHNAAR QNGGTQLPPQ FQPPRPNVPN
HMLSHPNGLQ DIMQQDPLGR LQGLDISKGP LVVKSESSSI
SASESSSTF
```

The invention claimed is:

1. A method of achieving constitutive expression of a gene of interest in plant cells, which comprises:
   (i) transforming the plant cells with a first nucleic acid sequence that comprises the gene of interest operably linked to a RTBV promoter,
   (ii) transforming the plant cells with a second nucleic acid sequence conferring the constitutive expression of (SEQ ID NO: 1) the coding sequence for Rf2a, and
   (iii) growing the plant cells, wherein said constitutive expression of the gene of interest is achieved in the plant cells.

2. The method of claim 1, wherein the plant cells are not rice cells.

3. A plant transformation vector, capable of transforming plant cells to achieve constitutive expression of a gene of interest, comprising (i) a RTBV promoter operably linked to the gene of interest and (ii) a constitutive promoter operably linked to a Rf2a encoding sequence.

4. The vector of claim 3, wherein the constitutive promoter is a CaMV 35S promoter.

5. The vector of claim 3, wherein the plant cells are not rice cells.

6. A set of plant transformation vectors, capable of transforming plant cells to achieve constitutive expression of a gene of interest, comprising (i) a first vector comprising a RTBV promoter operably linked to the gene of interest and (ii) a second vector comprising a constitutive promoter operably linked to a Rf2a encoding sequence.

7. The vector of claim 6, wherein the constitutive promoter is a CaMV 35S promoter.

8. The vector of claim 6, wherein the plant cells are not rice cells.

* * * * *

SEQUENCE LISTING

```
<160> NUMBER OF SEQ ID NOS: 12

<210> SEQ ID NO 1
<211> LENGTH: 368
<212> TYPE: PRT
<213> ORGANISM: Oryza sp.

<400> SEQUENCE: 1

Met Asn Arg Glu Lys Ser Pro Ile Pro Gly Asp Gly Asp Gly Leu
1               5                   10                  15

Pro Pro Gln Ala Thr Arg Arg Ala Gly Pro Pro Ala Ala Ala Ala
              20                  25                  30

Ala Glu Tyr Asp Ile Ser Arg Met Pro Asp Phe Pro Thr Arg Asn Pro
            35                  40                  45

Gly His Arg Arg Ala His Ser Glu Ile Leu Ser Leu Pro Glu Asp Leu
      50                  55                  60

Asp Leu Cys Ala Ala Gly Gly Asp Gly Pro Ser Leu Ser Asp Glu
65                  70                  75                  80

Asn Asp Glu Glu Leu Phe Ser Met Phe Leu Asp Val Glu Lys Leu Asn
                85                  90                  95

Ser Thr Cys Gly Ala Ser Ser Glu Ala Glu Ala Glu Ser Ser Ser Ala
            100                 105                 110

Ala Ala His Gly Ala Arg Pro Lys His Gln His Ser Leu Ser Met Asp
```

```
                115                 120                 125
Glu Ser Met Ser Ile Lys Ala Glu Glu Leu Val Gly Ala Ser Pro Gly
    130                 135                 140

Thr Gly Met Ser Ser Ala Glu Ala Lys Lys Ala Val Ser Ala Val
145                 150                 155                 160

Lys Leu Ala Glu Leu Ala Leu Val Asp Pro Lys Arg Ala Lys Arg Ile
                165                 170                 175

Trp Ala Asn Arg Gln Ser Ala Ala Arg Ser Lys Glu Arg Lys Met Arg
                180                 185                 190

Tyr Ile Ala Glu Leu Glu Arg Lys Val Gln Thr Leu Gln Thr Glu Ala
                195                 200                 205

Thr Thr Leu Ser Ala Gln Leu Ala Leu Leu Gln Arg Asp Thr Ser Gly
    210                 215                 220

Leu Thr Thr Glu Asn Ser Glu Leu Lys Leu Arg Leu Gln Thr Met Glu
225                 230                 235                 240

Gln Gln Val His Leu Gln Asp Ala Leu Asn Asp Thr Leu Lys Ser Glu
                245                 250                 255

Val Gln Arg Leu Lys Val Ala Thr Gly Gln Met Ala Asn Gly Gly Gly
                260                 265                 270

Met Met Met Asn Phe Gly Gly Met Pro His Gln Phe Gly Gly Asn Gln
    275                 280                 285

Gln Met Phe Gln Asn Asn Gln Ala Met Gln Ser Met Leu Ala Ala His
    290                 295                 300

Gln Leu Gln Gln Leu Gln Leu His Pro Gln Ala Gln Gln Gln Gln Val
305                 310                 315                 320

Leu His Pro Gln His Gln Gln Gln Pro Leu His Pro Leu Gln Ala
                325                 330                 335

Gln Gln Leu Gln Gln Ala Ala Arg Asp Leu Lys Met Lys Ser Pro Met
                340                 345                 350

Gly Gly Gln Ser Gln Trp Gly Asp Gly Lys Ser Gly Ser Ser Gly Asn
                355                 360                 365

<210> SEQ ID NO 2
<211> LENGTH: 329
<212> TYPE: PRT
<213> ORGANISM: Oryza sp.

<400> SEQUENCE: 2

Met Gln Glu Pro Lys His Thr Asp Pro Ala Ala Met Arg Gly Ala His
1               5                   10                  15

His Arg Arg Ala Arg Ser Glu Val Ala Phe Arg Leu Pro Asp Asp Leu
                20                  25                  30

Asp Leu Gly Gly Gly Ala Gly Ala Phe Asp Glu Ile Gly Ser Glu
            35                  40                  45

Asp Asp Leu Phe Ser Thr Phe Met Asp Ile Glu Lys Ile Ser Ser Gly
            50                  55                  60

Pro Ala Ala Gly Gly Ser Asp Arg Asp Arg Ala Ala Glu Thr Ser
65                  70                  75                  80

Ser Pro Pro Arg Pro Lys His Arg His Ser Ser Ser Val Asp Gly Ser
                85                  90                  95

Gly Phe Phe Ala Ala Ala Arg Lys Asp Ala Ala Ala Ser Leu Ala Glu
                100                 105                 110

Val Met Glu Ala Lys Lys Ala Met Thr Pro Glu Gln Leu Ser Asp Leu
            115                 120                 125
```

-continued

```
Ala Ala Ile Asp Pro Lys Arg Ala Lys Arg Ile Leu Ala Asn Arg Gln
            130                 135                 140

Ser Ala Ala Arg Ser Lys Glu Arg Lys Ala Arg Tyr Ile Thr Glu Leu
145                 150                 155                 160

Glu Arg Lys Val Gln Thr Leu Gln Thr Glu Ala Thr Thr Leu Ser Ala
                165                 170                 175

Gln Leu Thr Leu Phe Gln Arg Asp Thr Thr Gly Leu Ser Ala Glu Asn
            180                 185                 190

Ala Glu Leu Lys Ile Arg Leu Gln Ala Met Glu Gln Gln Ala Gln Leu
        195                 200                 205

Arg Asp Ala Leu Asn Asp Ala Leu Lys Gln Glu Leu Glu Arg Lys Leu
    210                 215                 220

Lys Ala Thr Gly Glu Met Thr Asn Ser Asn Glu Thr Tyr Ser Met Gly
225                 230                 235                 240

Leu Gln His Val Pro Tyr Asn Thr Pro Phe Phe Pro Leu Ala Gln His
                245                 250                 255

Asn Ala Ala Arg Gln Asn Gly Gly Thr Gln Leu Pro Pro Gln Phe Gln
            260                 265                 270

Pro Pro Arg Pro Asn Val Pro His Met Leu Ser His Pro Asn Gly
        275                 280                 285

Leu Gln Asp Ile Met Gln Asp Pro Leu Gly Arg Leu Gln Gly Leu
    290                 295                 300

Asp Ile Ser Lys Gly Pro Leu Val Val Lys Ser Glu Ser Ser Ile
305                 310                 315                 320

Ser Ala Ser Glu Ser Ser Ser Thr Phe
                325
```

<210> SEQ ID NO 3
<211> LENGTH: 36
<212> TYPE: DNA
<213> ORGANISM: Artificial Sequence
<220> FEATURE:
<223> OTHER INFORMATION: Primer

<400> SEQUENCE: 3
gccgcccata tggagaagat gaacagggag aaatcc            36

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
cgcggatcct cagttgccgc tgcttcctga            30

<210> SEQ ID NO 5
<211> LENGTH: 35
<212> TYPE: DNA
<213> ORGANISM: Artificial Sequence
<220> FEATURE:
<223> OTHER INFORMATION: Primer

<400> SEQUENCE: 5
gccgcccata tggagaagat gtccgccgcc gccca            35

<210> SEQ ID NO 6
<211> LENGTH: 30
<212> TYPE: DNA

<213> ORGANISM: Artificial Sequence
<220> FEATURE:
<223> OTHER INFORMATION: Primer

<400> SEQUENCE: 6
cgcggatcct cagtgtggca tgccaccgaa                30

<210> SEQ ID NO 7
<211> LENGTH: 64
<212> TYPE: PRT
<213> ORGANISM: Oryza sp.

<400> SEQUENCE: 7

Asp Pro Lys Arg Ala Lys Arg Ile Ile Ala Asn Arg Gln Ser Ala Ala
1               5                   10                  15

Arg Ser Lys Glu Arg Lys Ala Arg Tyr Ile Leu Glu Leu Glu Arg Lys
            20                  25                  30

Val Gln Thr Leu Gln Thr Glu Ala Thr Thr Leu Ser Ala Gln Leu Ser
        35                  40                  45

Leu Phe Gln Arg Asp Thr Thr Gly Leu Ser Ser Glu Asn Thr Glu Leu
    50                  55                  60

<210> SEQ ID NO 8
<211> LENGTH: 64
<212> TYPE: PRT
<213> ORGANISM: Oryza sp.

<400> SEQUENCE: 8

Asp Pro Lys Arg Ala Lys Arg Ile Leu Ala Asn Arg Gln Ser Ala Ala
1               5                   10                  15

Arg Ser Lys Glu Arg Lys Thr Arg Tyr Ile Phe Glu Leu Glu Arg Lys
            20                  25                  30

Val Gln Thr Leu Gln Thr Glu Ala Thr Thr Leu Ser Ala Gln Leu Thr
        35                  40                  45

Leu Leu Gln Arg Asp Thr Asn Gly Leu Thr Val Glu Asn Asn Glu Leu
    50                  55                  60

<210> SEQ ID NO 9
<211> LENGTH: 64
<212> TYPE: PRT
<213> ORGANISM: Oryza sp.

<400> SEQUENCE: 9

Asp Pro Lys Arg Ala Lys Arg Ile Leu Ala Asn Arg Leu Ser Ala Ala
1               5                   10                  15

Arg Ser Lys Glu Arg Lys Thr Arg Tyr Ile Ser Glu Leu Glu His Lys
            20                  25                  30

Val Gln Lys Leu Gln Thr Glu Thr Thr Thr Leu Ser Thr Gln Val Thr
        35                  40                  45

Ile Leu Gln Lys Asn Phe Val Glu Ile Ser Ser Leu Asn Ser Glu Leu
    50                  55                  60

<210> SEQ ID NO 10
<211> LENGTH: 64
<212> TYPE: PRT
<213> ORGANISM: Oryza sp.

<400> SEQUENCE: 10

Glu Leu Lys Arg Glu Lys Arg Lys Gln Ser Asn Arg Glu Ser Ala Arg
1               5                   10                  15

-continued

```
Arg Ser Arg Leu Arg Lys Gln Ala Glu Thr Glu Leu Ala Thr Gln
            20                  25                  30

Val Glu Ser Leu Ala Ala Glu Asn Thr Ser Leu Arg Ser Glu Ile Gly
        35                  40                  45

Arg Leu Thr Glu Ser Ser Glu Lys Leu Arg Leu Ala Asn Ser Ala Leu
    50                  55                  60

<210> SEQ ID NO 11
<211> LENGTH: 64
<212> TYPE: PRT
<213> ORGANISM: Oryza sp.

<400> SEQUENCE: 11

Glu Glu Arg Val Arg Lys Arg Lys Glu Ser Asn Arg Glu Ser Ala Arg
1               5                   10                  15

Arg Ser Arg Tyr Arg Lys Ala Ala His Leu Lys Glu Leu Glu Asp Gln
            20                  25                  30

Val Ala Gln Leu Lys Ala Glu Asn Ser Cys Leu Leu Arg Arg Ile Ala
        35                  40                  45

Ala Leu Asn Gln Lys Tyr Asn Asp Ala Asn Val Asp Asn Arg Val Leu
    50                  55                  60

<210> SEQ ID NO 12
<211> LENGTH: 64
<212> TYPE: PRT
<213> ORGANISM: Oryza sp.

<400> SEQUENCE: 12

Val Glu Lys Val Leu Arg Arg Leu Ala Gln Asn Arg Glu Ala Ala Arg
1               5                   10                  15

Lys Ser Arg Leu Arg Lys Lys Ala Tyr Val Gln Gln Leu Glu Asn Ser
            20                  25                  30

Lys Leu Lys Leu Ile Gln Leu Glu Gln Glu Leu Glu Arg Ala Arg Lys
        35                  40                  45

Gln Gly Met Cys Val Gly Gly Val Asp Ala Ser Gln Leu Ser Tyr
    50                  55                  60
```